United States Patent [19]

Szyszkowski

[11] Patent Number: 5,775,346
[45] Date of Patent: Jul. 7, 1998

[54] INTERPROXIMAL DENTAL APPLIANCES

[75] Inventor: Andrew J. Szyszkowski, Canyon Country, Calif.

[73] Assignee: Advanced Implant Technologies Inc., Beverly Hills, Calif.

[21] Appl. No.: 844,004

[22] Filed: Apr. 18, 1997

Related U.S. Application Data

[63] Continuation-in-part of Ser. No. 601,085, Feb. 14, 1996, abandoned.

[51] Int. Cl.$^6$ ...................................................... A61C 15/00
[52] U.S. Cl. .......................... 132/329; 132/321; 433/142
[58] Field of Search .................................. 433/141, 142, 433/216; 132/321, 323, 329

[56] References Cited

U.S. PATENT DOCUMENTS

| | | | |
|---|---|---|---|
| 1,833,555 | 11/1931 | Bell et al. | 433/142 |
| 1,840,484 | 1/1932 | Brown | 433/143 |
| 1,913,598 | 6/1933 | Keefe | 433/142 |
| 3,511,249 | 5/1970 | Baitz | 132/329 |
| 3,775,848 | 12/1973 | Barnett | 433/142 |
| 3,779,256 | 12/1973 | Maloney et al. | |
| 4,280,518 | 7/1981 | Gambaro | |
| 4,449,933 | 5/1984 | Forni | |
| 4,660,583 | 4/1987 | Brown | |
| 4,805,646 | 2/1989 | Shimenkov | |
| 4,832,061 | 5/1989 | Hwang | |
| 4,832,063 | 5/1989 | Smole | 132/329 |
| 4,911,187 | 3/1990 | Castillo | |
| 4,922,936 | 5/1990 | Buzzi et al. | |
| 4,974,615 | 12/1990 | Doundoulakis | 132/321 |
| 5,044,041 | 9/1991 | Ljungberg | |
| 5,063,948 | 11/1991 | Lloyd | 132/321 |
| 5,386,840 | 2/1995 | Lane | |
| 5,433,226 | 7/1995 | Burch | 132/321 |

FOREIGN PATENT DOCUMENTS

| | | |
|---|---|---|
| 236232 | 9/1987 | European Pat. Off. |
| 2016931 | 9/1979 | United Kingdom |

Primary Examiner—Ralph A. Lewis
Attorney, Agent, or Firm—Kelly Bauersfeld; Lowry & Kelley, LLP

[57] ABSTRACT

Interproximal dental appliances in the form of a floss-type linear media, a pick-type interproximal dental cleaner/tissue stimulator and an interproximal brush, include an elongated base and a plurality of elastomeric flat-faced flanges extending perpendicularly outwardly from the base in a staggered pattern to form a ribbed segment. A handle is provided adjacent to the ribbed segment, and an exteriorly smooth threaded leader or tip formed of a portion of the base extends away from the ribbed segment opposite the handle. The flanges include a first set of flanges spaced from one another along a longitudinal axis of the base and radially aligned with one another about the longitudinal axis, and a second set of radially aligned flanges longitudinally disposed in an alternating manner between adjacent flanges of the first set, wherein the first set of flanges is radially offset from the second set of flanges. Moreover, in some embodiments the base comprises a bi-material composite structure that includes a relatively stiff, resilient core and a sheath over the core integrally formed with the flanges.

31 Claims, 5 Drawing Sheets

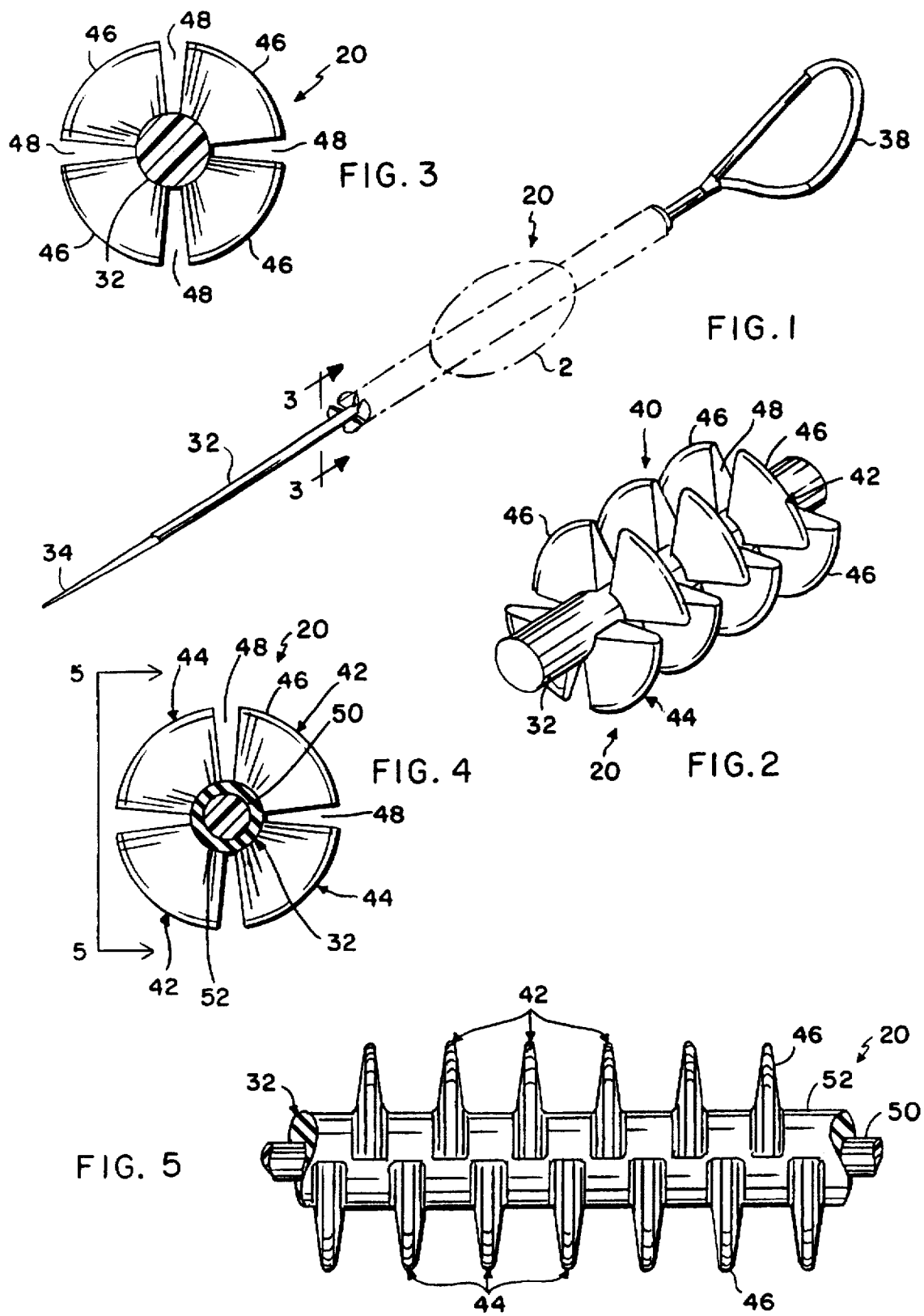

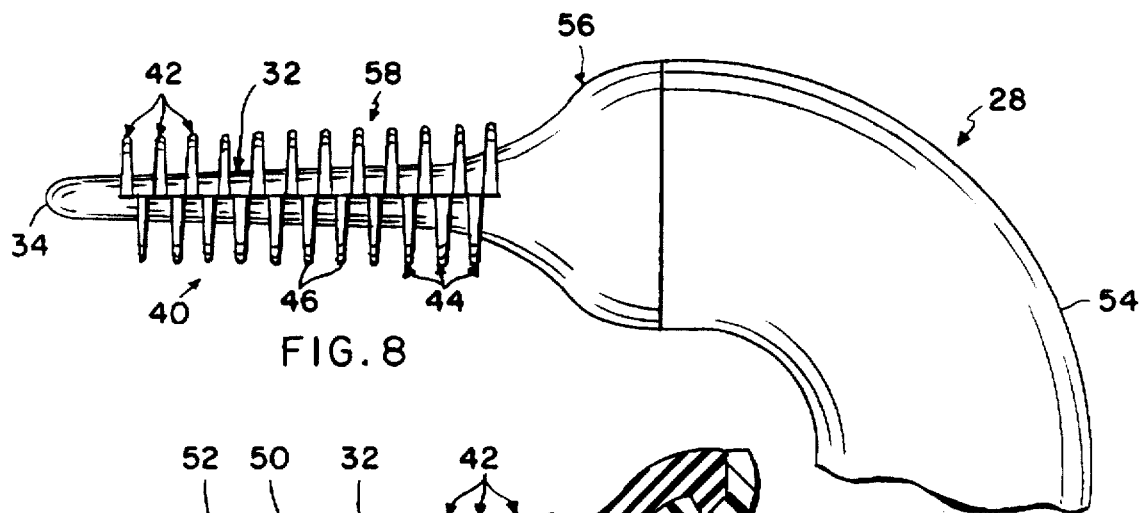
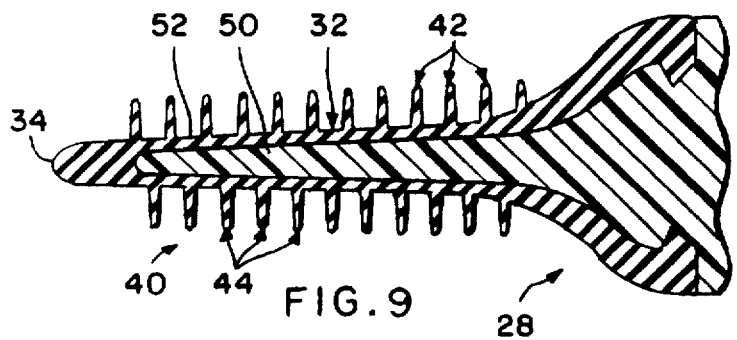
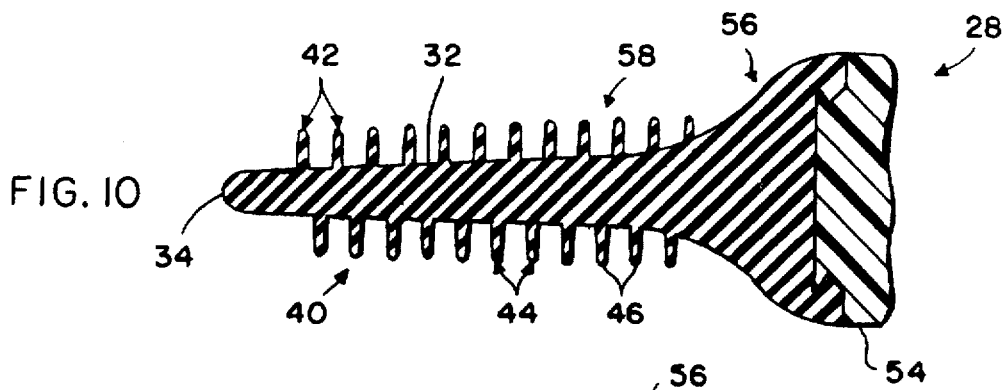
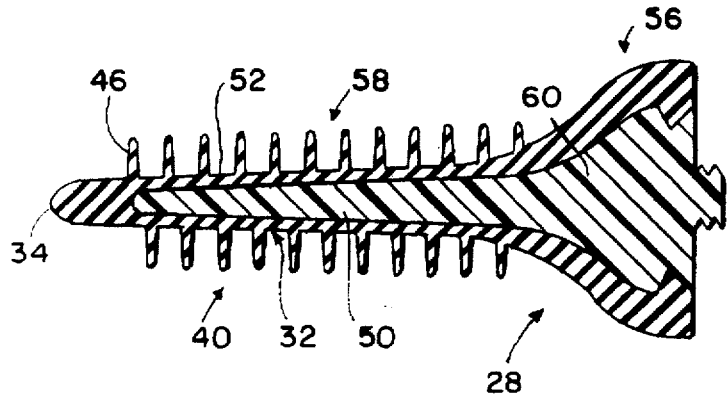

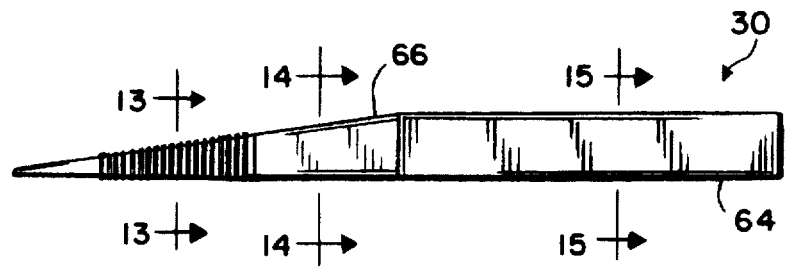
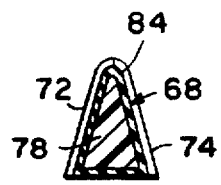
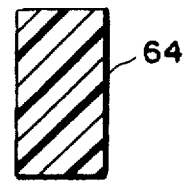
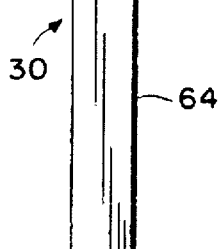
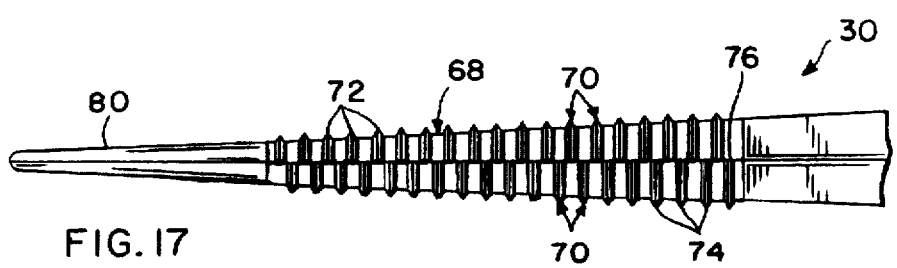
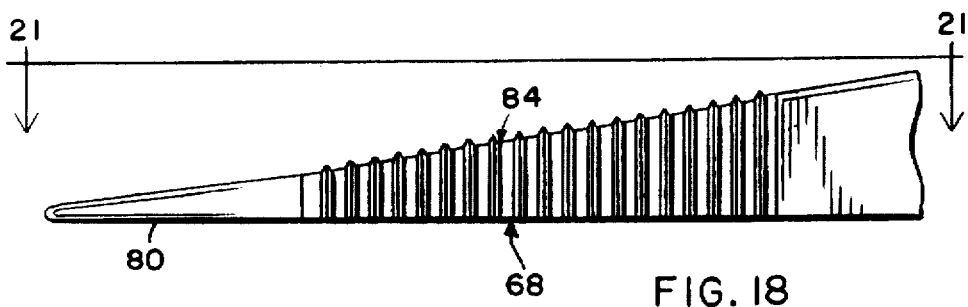

INTERPROXIMAL DENTAL APPLIANCES

RELATED APPLICATION

This is a continuation-in-part application of U.S. patent application Ser. No. 08/601,085, filed Feb. 14, 1996 and entitled INTERPROXIMAL DENTAL APPLIANCES, now abandoned..

BACKGROUND OF THE INVENTION

This invention relates generally to dental appliances. More specifically, the present invention relates to interproximal dental appliances such as floss-type linear media for cleaning bridges and implants, pick-type interproximal dental cleaners/tissue stimulators, and interproximal brushes. Yet more specifically, the present invention relates to molded polymer interproximal dental appliances of the type described above.

The general structure of teeth and gums in the human mouth takes the form of abutting tooth structures partially embedded in bone with the interproximal region between adjacent teeth being generally filled with gingival papilla or gum structure. Where there has been periodontal surgery or periodontal disease, the gingival papilla and bone structure, which formerly filled the interproximal region, will have deteriorated significantly. The result is an interproximal space which provides an excellent environment for accumulation of food particles and the build up of bacteria and plaque. A vertical cross-sectional view of this interproximal space resembles a triangle in the region above the undiseased gum line. Below the gum line, the interproximal space resembles furrows extending along each tooth root and separated by a mound of gingival papilla. These furrows of space are referred to as the dental "sulcus" between a tooth and adjacent gingival papilla.

It is common knowledge that the build-up of plaque on the surface of a tooth is a significant contributor to tooth decay as well as associated tooth and gum diseases. The brushing of one's teeth with the standard toothbrush is often recognized as being inadequate to remove plaque from all surfaces of a tooth, especially those surfaces facing an adjacent tooth as well as those surfaces in the dental sulcus between the tooth and the interproximal gingival papilla. Moreover, it is beneficial to gently stimulate the gum tissue surrounding the teeth but, once again, the brushing of one's teeth with the standard toothbrush often provides insufficient tissue stimulation for optical oral health.

Dental appliances specialized for cleaning interproximal spaces are well known as useful tools in plaque removal and tissue stimulation. Various woven, twisted or bonded fiber floss-type linear media are available for cleaning dental bridges and implants. The cleaning effectiveness of these traditional products tends to be limited because the cross-sectional area of these products tends to be reduced when tension is applied. Consequently, traditional fiber-based products have a limited capability in reaching and cleaning areas under bridges and implant prostheses that may be concave or which may have irregular surface contours. Further, fiber-based products tend to snag and fray or shred on sharp edges in the mouth.

Pick-type interproximal dental cleaners/tissue stimulators typically include a tapered point for cleaning interproximal spaces between the teeth and stimulating soft tissue in the interproximal space. These products are of three basic types: (1) soft wood; (2) hard molded plastic; and (3) molded rubber. Soft wood interproximal cleaners/stimulators lack durability and tend to soften, splinter, fray and break after being used in the mouth for a relatively short period of time. These products may also lack the strength necessary to be pushed into restricted interproximal spaces. The natural material utilized can demonstrate considerable variation in hardness and strength from item to item. Hard plastic interproximal cleaners/stimulators, on the other hand, typically have sharp points and sharp edges that can injure soft tissue if used carelessly or aggressively. Further, the lack of flexibility of these products severely limits their ability to clean interproximal tooth surfaces. Traditional molded rubber tips are primarily beneficial for soft tissue stimulation and are not effective for thorough plaque removal.

Prior art interproximal brushes typically comprise fine nylon bristles retained by a twisted wire core. The brushes have a round cross-section and may be cylindrical or conical in profile. Interproximal brushes are typically of several basic types: (1) a brush set at a 90° to 100° angle to a handle similar to a toothbrush handle; and (2) a small, straight interproximal brush about 2.5 inches long with a handle normally held between the thumb and one or two fingers; (3) tufted brushes such as the Sulca Brush™; and (4) plastic foam brushes comprising a plastic inner stem and an outer soft foam cover. The twisted core wires of many contemporary brushes are coated with Teflon to prevent imitation of the nerves of teeth caused by small electrical voltages generated in the mouth when the dissimilar metals used in the brush core wires and dental restorations respectively create a battery-effect in the acid environment of the mouth. The cores of such prior art brushes are capable of withstanding very limited bending forces, the brush bristles lack durability, and the replaceable interproximal brushes used with toothbrush-style handles must be changed frequently. Placing a new brush into an existing handle is typically inconvenient and time consuming. In some products, the stem end of the brush tends to protrude from the back of the handle and must be carefully bent down or to the side to avoid leaving a protrusion that can irritate or even penetrate tissues inside of the lips or cheek. The core of the brush presents many small crevices that can be penetrated by micro-organisms. If, as is frequently the case, a brush is used to clean periodontally infected areas, the porous quality of the brush has the potential to contribute to periodontal infections in previously uninfected areas of the mouth.

The foregoing and other limitations and shortcomings in products for cleaning interdental or interproximal spaces of the traditional prior art have been widely recognized for many years. Various inventors have developed numerous inventions in the attempt to overcome the limitations of the traditional prior art. See, for example, U.S. Pat. Nos. 4,660, 583; 4,911,187; and 4,280,518.

While each of these inventions offers one or more novel features directed at overcoming the limitations or shortcomings of the traditional prior art, each of these products present, individually and collectively, limitations that fail to satisfy all of the criteria for a clinically effective interdental cleaning product necessary for gaining wide acceptance by dental professionals and dental patients.

Specifically, there are four key criteria that a truly effective oral hygiene product for interdental cleaning must satisfy:

1. The product must be effective in removing plaque and debris from the varied and often geometrically complex surfaces of natural tooth structure and various dental prosthesis such as bridges and implants.
2. The product must be safe to use without causing undue irritation or injury to normal, post-surgical or even periodontally infected soft tissues.

3

3. The product must be capable of effectively adapting to and cleaning interdental spaces of the widest possible range of sizes and geometrical configurations. Such variations exist both among patients and, in most cases, within the conditions presented by the dentition of a single patient. No single product is likely to be ideal for every possible interdental configuration. However, the restriction of a product's applicability to a narrow range of interdental space sizes or interdental space geometrical configurations will greatly limit its clinical usefulness and its attractiveness to either dental professionals or dental patients.

4. The product must be capable of being manufactured economically.

Accordingly, there continues to be a need for novel appliances for cleaning interproximal spaces that both overcome the limitations and shortcomings of the traditional prior art and satisfy the four criteria for effective interdental cleaning products listed above. The present invention fulfills these needs and provides other related advantages.

SUMMARY OF THE INVENTION

The present invention resides in molded polymer interproximal dental appliances which overcome the above-noted drawbacks of the prior art. The interproximal dental appliances of the present invention comprise, generally, a handle at one end of the dental appliance, and an interproximal dental cleaner that extends from the handle to a threaded leader or tip. The dental cleaner includes a ribbed segment which comprises a plurality of elastomeric, flat-faced flanges which extend perpendicularly outwardly from a base in a staggered pattern.

More particularly, the flanges include a first set which are spaced from one another along a longitudinal axis of the base and which are radially aligned with one another about said longitudinal axis, and a radially aligned second set which are longitudinally disposed in an alternating manner between adjacent flanges of the first set, wherein the first set of flanges is radially offset from the second set of flanges. In some of the illustrated embodiments each flange of the first and second sets comprises a plurality of spaced-apart flange sections which extend co-planarly from the base. More specifically, each flange may be divided radially into two or more sections which extend perpendicularly outwardly from the base on opposite sides thereof in order to increase adaptability of the appliance to the geometry of interproximal spaces. The flange sections of the second set of flanges are generally radially aligned with spaces between the flange sections of the first set of flanges to better obtain the desired cleaning/stimulation effect of the interproximal dental appliance when in use.

The base may comprise a bi-material composite structure that includes a relatively stiff, resilient core, and a softer, flexible sheath over the core which is integrally formed with the flanges. The typically elastomeric sheath may encapsulate an end of the core to form a flexible leader that is threadable into the interproximal spaces between the teeth. The sheath may be attached to the core utilizing an adhesive or solvent bond.

In one preferred form of the invention, the interproximal dental appliance includes an elongated base and a plurality of flanges which extend perpendicularly outwardly from the base to collectively form a generally cylindrical ribbed segment in a bridge cleaner or floss-type interproximal dental appliance. A handle is formed of a closed loop portion of the base, and an exteriorly smooth tip or threadable leader

4 is formed of a portion of the base extending away from the ribbed segment opposite the handle. At least a portion of the base and the flanges are integrally molded of an elastomeric polymer. As shown, the flanges are staggered in an alternating pattern.

In other preferred forms of the invention, the interproximal dental appliance includes an elongated, generally frusto-conical base, and a plurality of flanges which extend perpendicularly outwardly from the base in a staggered, alternating pattern to collectively form a generally frusto-conical ribbed segment. A handle is provided adjacent to the ribbed segment, and an exteriorly smooth tip is formed of a portion of the base extending away from the ribbed segment opposite the handle. More specifically, in a pick-type interproximal dental cleaner/tissue stimulator, the flanges and the base are generally triangular in cross-section. With regard to an interproximal brush, the flanges and the base are generally circular in cross-section. In this particular embodiment the handle extends generally perpendicularly to a longitudinal axis of the base.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a floss-type linear media for cleaning bridges and implants, embodying the present invention;

FIG. 2 is an enlarged, fragmented perspective view of a generally cylindrical ribbed segment comprising a plurality of elastomeric flat-faced flanges extending perpendicularly outwardly from a base in a staggered, alternating pattern, taken generally of the area indicated by the number 2 in FIG. 1;

FIG. 3 is an enlarged sectional view taken generally along the line 3—3 of FIG. 1;

FIG. 4 is a sectional view similar to that shown in FIG. 3, illustrating an alternative embodiment wherein the base comprises a bi-material composite structure including a relatively flexible, high modulus of elasticity core for stability in resisting axial tensile forces and a relatively soft, flexible sheath over the core integrally formed with the flanges;

FIG. 5 is a fragmented, partially sectional elevational view taken generally along the line 5—5 of FIG. 4;

FIG. 8 is an enlarged, partially fragmented elevational view of a head for an interproximal brush embodying the present invention;

FIG. 9 is a fragmented vertical section of the head for the interproximal brush of FIG. 8 showing a bi-material composite structure;

FIG. 10 is a vertical cross-sectional view similar to that illustrated in FIG. 9, illustrating an alternative embodiment wherein the head is comprised of a monolithic structure bonded directly to a hard polymer handle, wherein the head, like that in FIG. 9, includes a plurality of elastomeric flat-faced flanges extending perpendicularly outwardly from a base in a staggered pattern, the flanges including a first set spaced from one another along a longitudinal axis of the base and radially aligned with one another about said longitudinal axis, and a radially aligned second set longitudinally disposed in an alternating manner between adjacent flanges of the first set along the longitudinal axis of the base, wherein the first set of flanges is radially offset from the second set of flanges;

FIG. 11 is a vertical section similar to those illustrated in FIGS. 9 and 10, illustrating yet another alternative embodiment wherein the head includes a spine-like element that reinforces an elastomeric tip and which is fabricated as a separate piece that is inserted into a socket molded into the handle;

FIG. 12 is an elevational view of a pick-type interproximal dental cleaner/tissue stimulator, embodying the present invention;

FIG. 13 is an enlarged sectional view taken generally along the line 13—13 of FIG. 12;

FIG. 14 is an enlarged sectional view taken generally along the line 14—14 of FIG. 12;

FIG. 15 is an enlarged sectional view taken generally along the line 15—15 of FIG. 12;

FIG. 16 is an exploded elevational view of the pick-type interproximal dental cleaner/tissue stimulator shown in FIG. 12, wherein an elastomeric sheath is shown removed from an underlying core portion of a base;

FIG. 17 is a top plan view of the interproximal dental cleaner/tissue stimulator of FIG. 12;

FIG. 18 is an enlarged, fragmented elevational view of a pick portion of the dental cleaner/tissue stimulator of FIG. 12;

DETAILED DESCRIPTION OF THE PREFERRED EMBODIMENTS

Figure 6:
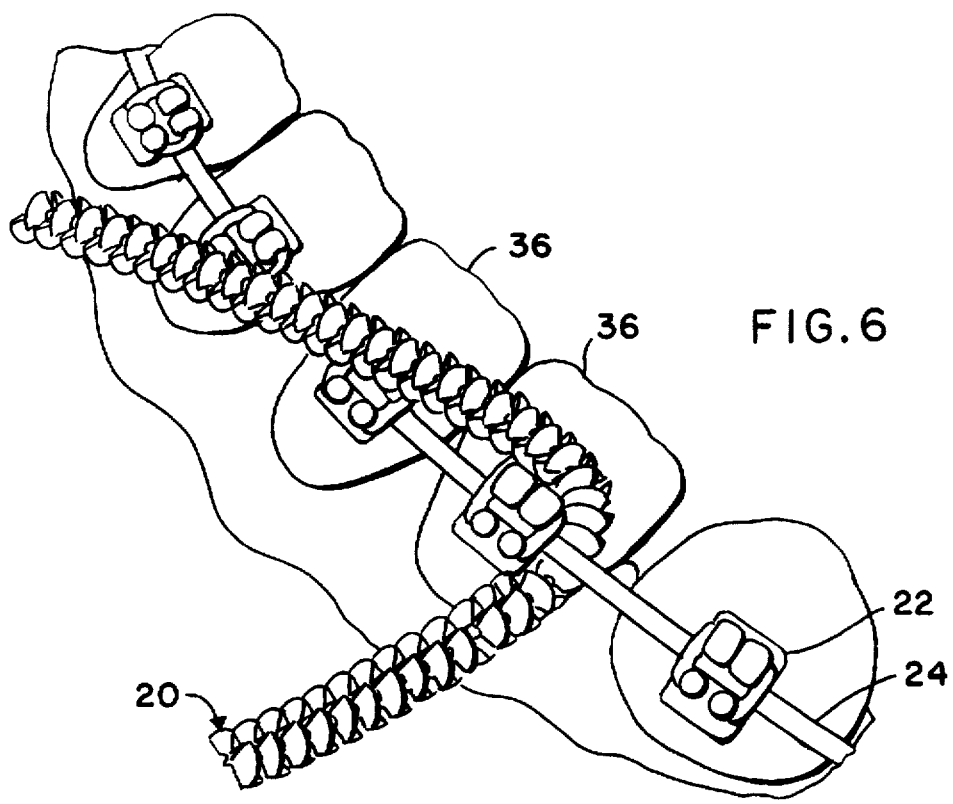
FIG. 6 is an environmental illustration showing the flexibility of the floss-type linear media of FIGS. 1–5 which permits it to be contoured around orthodontic brackets and wires.
Figure 7:
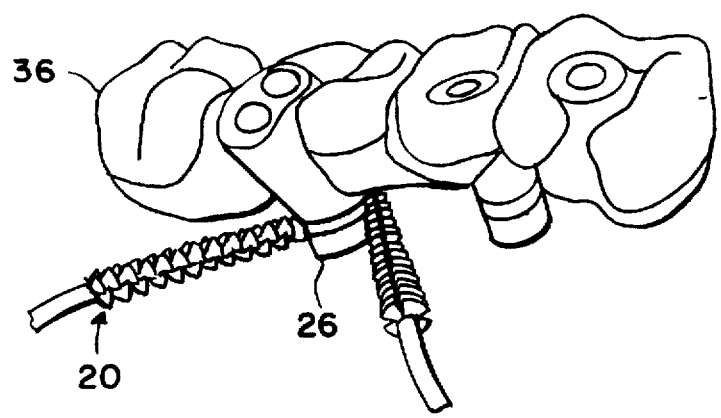
FIG. 7 is another environmental illustration of the floss-type linear media of FIGS. 1–5, illustrating the manner in which it may be contoured around implant abutments.
Figure 19:
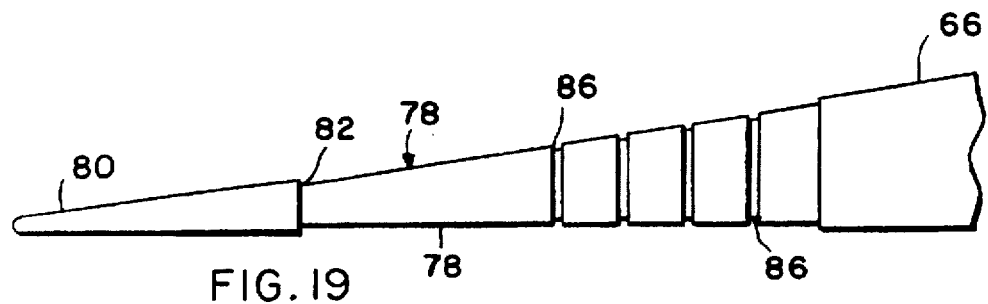
FIG. 19 is a fragmented elevational view similar to that shown in FIG. 18, wherein a flange-bearing sheath has been removed therefrom.
Figure 20:
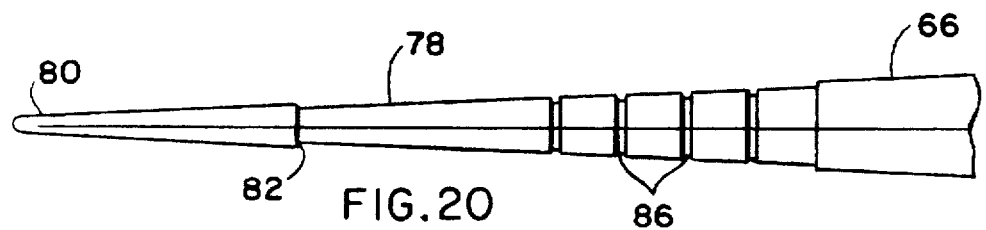
FIG. 20 is a top plan view of the structure illustrated in FIG. 19.
Figure 21:
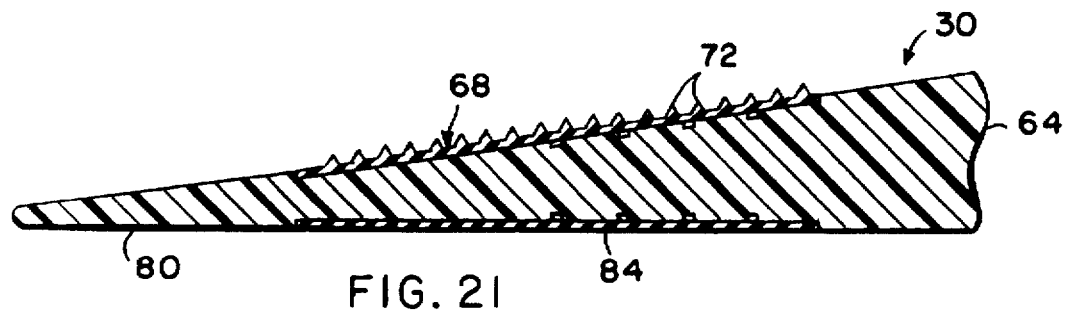
FIG. 21 is a sectional view taken along the longitudinal axis 30 of the base and generally along the line 21—21 of FIG. 18.

As shown in the drawings for purposes of illustration, the present invention is concerned with molded plastic interproximal dental appliances, generally designated in FIGS. 1–7 by the reference number 20 with respect to a molded plastic floss-type linear media (for cleaning bridges, around orthodontic brackets 22 and wires 24 (FIG. 6), or implant abutments 26 (FIG. 7)), in FIGS. 8–11 by the reference number 28 with respect to an interproximal brush, and in FIGS. 12–22 by the reference number 30 with respect to a pick-type interproximal dental cleaner/tissue stimulator. Each of the illustrated interproximal dental appliances 20, 28 and 30 is preferably molded of one or more nonporous elastomeric polymers that can be readily cleaned both during and after use to prevent the possible spread of periodontal infection in the mouth.

In accordance with the present invention and with reference to FIGS. 1–7, the floss-type linear media 20 includes an elongated, generally cylindrical base 32 having a threadable leader 34 or tip at one end configured for insertion into interproximal spaces between teeth 36, and a handle 38 at another end which comprises a closed loop of the base 32. A plurality of elastomeric flat-faced flanges 40 extend perpendicularly outwardly from the base 32 between the threadable leader 34 and the handle 38 in a staggered pattern. The flanges 40 include a first set 42 spaced from one another along a longitudinal axis of the base 32 and radially aligned with one another about said longitudinal axis, and a radially aligned second set 44 longitudinally disposed in an alternating manner between adjacent flanges of the first set 42 along the longitudinal axis of the base 32, wherein the first set 42 of flanges 40 is radially offset from the second set 44 of flanges 40.

Each flange 40 of the first and second sets 42 and 44 comprises a plurality of spaced-apart flange sections 46 which extend co-planarly from the base 32. In particular, each flange 40 of the first and second sets 42 and 44 comprises a pair of pie-shaped flange sections 46 which extend perpendicularly outwardly from the base 32 on opposite sides thereof. The flange sections 46 of the second set 44 are generally radially aligned with spaces between the flange sections 46 of the first set 42. Moreover, the first set 42 of flanges is radially offset from the second set 44 of flanges to form four longitudinally extending channel-like radial separations 48 therebetween. The flanges 40 collectively form a generally cylindrical ribbed segment in the floss-type linear media 20. In other words, the plurality of spaced-flange sections 46 of the first and second sets 42 and 44 can be seen as comprising, respectively, third and fourth sets of flanges, wherein the flanges in a respective set are spaced from one another along the longitudinal axis of the base and radially aligned with one another about said longitudinal axis. Each flange of the third set extends from the base co-planarly with a respective flange of the first set, and each flange of the fourth set extends from the base co-planarly with a respective flange of the second set. The flanges of the first and third sets are pie-shaped, and each respective co-planar pair of flanges extend from the base on opposite sides thereof. Similarly, the flanges of the second and fourth sets are pie-shaped, and each respective co-planar pair of flanges extend from the base on opposite sides thereof. The second and fourth sets of flanges are generally radially aligned with spaces between the first and third sets of flange sections.

Because interproximal embrasure (the spaces between teeth) vary from nonexistent to 5 to 6 mm or larger, one key to creating a successful interproximal cleaning device is its ability to work effectively in the widest possible range of aperture sizes. Many prior art devices are extremely limited or simply unworkable because of a lack of adaptability. Further, an important requirement for a useful device is the ability of the device to provide cleaning action without producing excessive irritation of soft tissues. It is believed that a majority of the dental patients who need to use interproximal cleaning devices suffer from periodontal disease and have unhealthy oral tissues that are tender and easily irritated. Cleaning action versus protection of soft tissues requires a trade-off, but hard plastic devices with sharp edges are not satisfactory. Additionally, hard plastic devices are typically not able to accommodate to the often complex and irregular geometry of natural tooth structure and dental prostheses or restorations.

The present invention, as illustrated in connection with the floss-type linear media of FIGS. 1–7, includes several features to improve adaptability to a wide range of interproximal aperture sizes and to minimize discomfort without compromising cleaning action. As described above, flat-faced flanges 40 which extend perpendicularly outwardly from the base 32 that are staggered in an alternating pattern, provide significant advantages over the prior art. The ribbed segment includes wedge-shaped radial separations 48 between flange sections 46 that essentially remove 10% to 20% of the material that would otherwise be required. The particular configuration of the flanges 40 improves both the ability of the dental appliance 20 to accommodate to irregularities in hard surface conditions and, by providing void spaces into which the flange sections can be deformed, allows the dental appliance to fit into smaller apertures than would otherwise be the case, thus greatly improving adaptability to interproximal apertures of various sizes.

The floss-type linear media 20 of FIGS. 1–7 is typically utilized by grasping both ends of the base 32 so that it can be drawn back and forth in the interdental space only by applying alternate tension. The looped handle 38 is, thus, provided only for pulling the dental appliance 20, and it is possible to insert one or two fingers through the soft, conformable loop to ensure a secure grip for this purpose. The loop handle 38 also serves a second important function, namely that of organizing several such dental appliances 20 in a package. By inserting a die-cut tongue on a packaging card through the loop handles 38 of ten to thirty or more appliances 20 in succession, the ordinarily unwieldy dental appliances 20 can be neatly aligned for display. This arrangement also makes it possible to easily dispense the dental appliances 20 from the package one at a time for use.

The floss-type linear media dental appliance 20 is preferably produced from a relatively high-tensile, relatively low durometer elastomeric polymer and molded as an integral unit. Alternatively, as illustrated in FIGS. 4 and 5, the base 32 may comprise a bi-material composite structure including a relatively stiff, resilient core 50, and a sheath 52 over the core which is integrally formed with the flanges 40. The cental core 50 could be a monofilamnent, twisted fiber or woven thread about which the sheath 52 and the flanges 40 are molded. It should be understood, however, that whether or not a core 50 is included as part of the base 32, the dental appliance 20 will remain flexible so as to easily contour around the orthodontic brackets 22 and wires 24 (FIG. 6) or the implant abutments 26 (FIG. 7), as well as between and around ones teeth 36.

With reference to FIGS. 8–11, the interproximal brush 28 is shown to include a handle portion 54 and a head portion 56. As was the case with the floss-type linear media 20 discussed above, the head portion 56 of the interproximal brush 28 includes an elongated base 32 configured for insertion into interproximal spaces between teeth 36, and a plurality of elastomeric flat-faced flanges 40 which extend perpendicularly outwardly from the base in a staggered pattern. The pattern and configuration of the flanges 40 is, in all material respects, the same as described above in detail in connection with the dental appliance embodiment shown in FIGS. 1–7, with the exception being that the flanges 40 collectively form a generally frusto-conical ribbed segment 58 about a base 32 that is also generally frusto-conical. Accordingly the description above in connection with the embodiment shown in FIGS. 1–7 relative to the base 32 and the flanges 40 applies fully to the various embodiments of the interproximal brush 28, and thus the same reference numbers are utilized in the drawings for the same elements common to both the floss-type linear media 20 and the interproximal brush 28.

FIGS. 8 and 9 illustrate one particular embodiment of the interproximal brush 28 wherein a bi-material composite structure is utilized within the head portion 56. The outer sheath 52 and the flanges 40 are formed of a relatively soft, deformable and elastic material which is fully bonded to a stiff, resilient polymer core 50 that provides resistance to the compressive, shear and bending moment forces generated by use. As shown, the core 50 is simply an extension of and integrally molded with the handle portion 54. As part of the bi-material composite structure, the outer elastic sheath 52, in conjunction with the adhesive bond, actually makes a not insignificant contribution to total resistance to bending and thus makes possible a small but highly significant reduction in the required diameter of the inner core 50 relative to what would be required with any known material soft enough to be brought into vigorous contact with soft tissues. While many potentially suitable polymers exist that may be utilized for both the sheath 52 and the core 50, it is most desirable to utilize materials which combine suitable mechanical properties, good manufacturing characteristics and relative economy. For the sheath 52 and flanges 40 the primary preferred polymers are Shore A hardness elastomeric urethanes or silicones in similar durometers. The primary polymers for the handle portion 54 and core 50 are "hard" (non-elastomeric) modified urethanes, modified ABS polymers and polypropylenes.

The sheath 52 encapsulates an end of the core 50 and forms a flexible leader 34, and is bonded to the core 50 utilizing any suitable adhesive. Presently it believe that the best are cyanacrylates and various anaerobics, especially the more flexible members of these families. Alternatively, it is possible to use solvent bonding when a flexible, elastomeric urethane outer sheath 52 is used in conjunction with a rigid, modified urethane core 50. Theoretically, solvent bonding provides the advantage of uniting the two urethane materials without introducing a third substance. The two different urethane based materials interpenetrate and merge within a narrow, amorphous zone. All volatile elements of the solvent migrate through the outer sheath and dissipate into the atmosphere. With solvent bonding it is anticipated that forces will be more uniformly distributed within the composite structure yielding an absence of stress concentrations.

FIG. 10 illustrates an alternative interproximal brush 28 having an outer configuration identical to that of the interproximal brush shown in FIGS. 8 and 9, the primary difference being that the base 32 and the flanges 40 are formed as an integral unit. There is no core 50 extending through a sheath 52. The flanges 40, however, retain the staggered and alternating pattern.

FIG. 11 illustrates yet another embodiment of the interproximal brush 28, again having the same external configuration as the interproximal brushes 28 of FIGS. 8 and 9, and FIG. 10. In the embodiment of FIG. 11 a small, spine-like element 60, formed separably from the head portion 56, provides the core 50 over which the sheath 52 is placed. The spine-like element 60 is configured for insertion into a socket 62 molded into the handle portion 54. This allows a manufacturer to use a less expensive and/or faster cycle time polymer for the handle portion 54 while selecting a polymer for the central spine-like element 60 with modulous, tensile strength yield properties that are more or less perfectly matched to the structural requirements for the head portion 56. For example, the handle portion 54 might be formed from a very inexpensive, fast cycle time polymer, and the spine-like element 60 might be manufactured from a high modulous, high-tensile strength, non-brittle polymer. Designs following this theory can yield smaller net outside diameters of the central core thus improving adaptability.

With reference to FIGS. 12-22, the pick-type cleaner/stimulator 30 includes a handle portion 64 and a pick portion 66. As shown in FIGS. 13-15, the pick portion includes an elongated, generally frusto-pyramidal base 68 which is generally triangular in cross section and, in contrast, the handle portion 64 is generally rectangular in cross-section. The triangular-sectioned pick embodiment 30 represents the application of the present invention to a traditional interproximal cleaning device geometry. The distinguishing features of the dental cleaner/tissue stimulator 30 of the present invention include the elastomeric flanges 70 which adjust to the widest possible range of interdental geometries and surface conditions, which flanges dislodge plaque and debris, trap it between the flanges, and remove it from the interdental space and from the mouth. Moreover, the soft elastomeric flanges 70 can stimulate and invigorate soft tissues with minimal danger of irritation or injury relative to stimulation by picks of hard material.

Although configured differently than the floss-type linear media 20 and the interproximal brush 28, the dental cleaner/tissue stimulator 30 of FIGS. 12-22 also includes an elongated base 68 configured for insertion into interproximal spaces between teeth 36, and a plurality of elastomeric flat-faced flanges 70 which extend perpendicularly outwardly from the base 68 in a staggered pattern. The flanges include a first set 72 spaced from one another along a longitudinal axis of the base 68 and radially aligned with one another about said longitudinal axis, and a radially aligned second set 74 longitudinally disposed in an alternating manner between adjacent flanges of the first set 72 along the longitudinal axis of the base, wherein the first set 72 of flanges is radially offset from the second set 74 of flanges.

In FIGS. 12-21, the pick portion 66 includes a central core 78 that forms a triangular tip 80 and, adjacent to the tip, a recessed portion 82 is provided in which a flange-bearing sheath 84 is positioned. The sheath 84 and the underlying core 78 form the base 68. Grooves 86 shown within the recess portion 82 of the core 78 are provided for mechanical retention of the sheath 84. The base 68 thus comprises a bi-material composite structure that includes a relatively stiff, resilient core 78, and a sheath 84 over the core 78 which is integrally formed with the flanges 70. The material characteristics of the sheath, flanges and underlying core of the dental cleaner/tissue stimulator 30 are the same as those discussed in connection with the interproximal brush 28.

Figure 22:
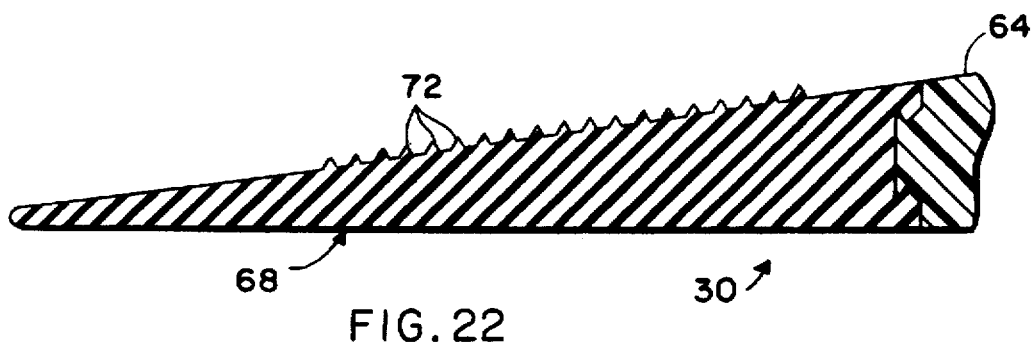
FIG. 22 is a sectional view similar to FIG. 21, illustrating an alternative embodiment wherein the end of the interproximal dental cleaner/tissue stimulator, including the threadable leader, is of a monolithic design and bonded to a relatively hard handle portion.

FIG. 22 illustrates an alternative embodiment of the dental cleaner/tissue stimulator 30 wherein the entire pick portion 66 is manufactured of a relatively soft elastomeric material that is adhered or attached to the handle portion 64 by means of a suitable mechanical or adhesive attachment. An analogous structure may be found in the interproximal bush 28 of FIG. 10.

The foregoing construction of the molded plastic interproximal dental appliances 20, 28 and 30 provides several advantages not realized in the prior art. With regard to the floss-type linear media 20, the molded construction thereof retains its cross-sectional configuration under tension. The molded flanges 40 that extend perpendicularly from the base 32 reach into concavities and irregular contours in the surface or supporting structure of bridge and implant prostheses. Moreover, the molded polymer product will not snag or fray.

The pick-type cleaner/stimulator 30 is durable and will last many times longer than typical wood or hard plastic items of the prior art. In addition, the flexible material used tends to conform to the shape of the interproximal space and to put firm, uniform pressure on the tooth surfaces in the interproximal space in a manner that aggressively disrupts plaque. The flanges 70 also tend to optimize plaque removal and aid in tissue stimulation. The slightly radiused edges and tip 80 of the pick-type cleaner/stimulator 30 preclude the possibility of cuts or other tissue damage. Moreover, the flexibility and elasticity of the pick-type cleaner/stimulator 30 provide the user with a greater range in working position relative to products of the prior art.

The interproximal brush 28, as noted above, is a molded unit that includes both brush and handle. The head portion 56 of this appliance comprises multiple staggered flanges 40 in the form of flange sections 46. These flange sections 46 are integrally molded with at least a portion of a tapered base 32 that provides flexibility at the tip 34 but greater stiffness and resistance to bending near the base of the head portion 56. Unlike conventional interproximal brush units comprised of a handle and a replaceable twisted wire brush element that can present an unprotected wire end, the interproximal brush 28 of the present invention is molded to include a smoothly contoured transition from the handle portion 54 to the head portion 56 that presents no comfort or safety hazard. The interproximal brush 28 is efficacious in removing plaque from interproximal tooth surfaces, for dislodging food particles trapped between the teeth and for stimulating interproximal soft tissues. The molded interproximal brush 28 is also many times more durable than twisted wire brushes.

Although several particular embodiments of the invention have been described in detail for purposes of illustration, various modifications of each may be made without departing from the spirit and scope of the invention. Accordingly, the invention is not to be limited, except as by the appended claims.

I claim:

1. An interproximal dental appliance, comprising:
    an elongated base configured for insertion into interproximal spaces between teeth; and
    a plurality of elastomeric flat-faced flanges extending perpendicularly outwardly from the base in a staggered pattern, the flanges including a first set spaced from one another along a longitudinal axis of the base and radially aligned with one another about said longitudinal axis, and a radially aligned second set longitudinally disposed in an alternating manner between adjacent flanges of the first set along the longitudinal axis of the base, wherein the first set of flanges is radially offset from the second set of flanges.

2. The dental appliance of claim 1, wherein the base includes a tapered threadable leader configured for insertion into interproximal spaces between teeth at one end and a handle at a second end, and wherein the elastomeric flanges extend from the base between the threadable leader and the handle.

3. The dental appliance of claim 2, wherein the flanges collectively form a generally cylindrical ribbed segment in a floss-type interproximal dental appliance.

4. The dental appliance of claim 3, wherein the base extends beyond the cylindrical ribbed segment to the handle and to the threadable leader, and wherein the handle comprises a closed loop of the base.

5. The dental appliance of claim 2, wherein the flanges collectively form a generally frusto-conical ribbed segment.

6. The dental appliance of claim 5, wherein the base is generally frusto-conical.

7. The dental appliance of claim 1, wherein the base comprises a bi-material composite structure including a relatively stiff, resilient core, and a sheath over the core integrally formed with the flanges.

8. The dental appliance of claim 7, wherein the sheath is bonded to the core utilizing an adhesive.

9. The dental appliance of claim 7, wherein the sheath is bonded to the core utilizing solvent bonding.

10. The dental appliance of claim 7, wherein the sheath encapsulates an end of the core and forms a flexible leader that is threadable into the interproximal spaces between teeth.

11. The dental appliance of claim 1, including a third set of flanges spaced from one another along the longitudinal axis of the base and radially aligned with one another about said longitudinal axis, wherein each flange of the third set extends from the base co-planarly with a respective flange of the first set.

12. The dental appliance of claim 11, wherein the flanges of the first and third sets are pie-shaped, and each respective co-planar pair of flanges extend from the base on opposite sides thereof.

13. The dental appliance of claim 11, including a fourth set of flanges spaced from one another along the longitudinal axis of the base and radially aligned with one another about said longitudinal axis, wherein each flange of the fourth set extends from the base co-planarly with a respective flange of the second set.

14. The dental appliance of claim 13, wherein the flanges of the second and fourth sets are pie-shaped, and each respective co-planar pair of flanges extend from the base on opposite sides thereof.

15. The dental appliance of claim 14, wherein the second and fourth sets of flanges are generally radially aligned with spaces between the first and third sets of flanges.

16. An interproximal dental appliance, comprising:
an elongated base including a threadable leader at one end configured for insertion into interproximal spaces between teeth, and a handle at a second end; and
a plurality of elastomeric flat-faced flanges extending perpendicularly outwardly from the base between the threadable leader and the handle in a staggered pattern, the flanges including a first set spaced from one another along a longitudinal axis of the base and radially aligned with one another about said longitudinal axis, and a radially aligned second set longitudinally disposed between adjacent flanges of the first set along the longitudinal axis of the base, wherein the first set of flanges is radially offset from the second set of flanges.

17. The dental appliance of claim 16, wherein the flanges collectively form a generally cylindrical ribbed segment in a floss-type interproximal dental appliance, wherein the base extends beyond the cylindrical ribbed segment to the handle and to the threadable leader, and wherein the handle comprises a closed loop of the base.

18. The dental appliance of claim 16, wherein the flanges collectively form a generally frusto-conical ribbed segment, and wherein the base is generally frusto-conical.

19. The dental appliance of claim 16, wherein the base comprises a bi-material composite structure including a relatively stiff, resilient core, and a sheath over the core integrally formed with the flanges.

20. The dental appliance of claim 19, wherein the sheath encapsulates an end of the core and forms the threadable leader.

21. The dental appliance of claim 16, including a third set of flanges spaced from one another along the longitudinal axis of the base and radially aligned with one another about said longitudinal axis, wherein each flange of the third set extends from the base co-planarly with a respective flange of the first set.

22. The dental appliance of claim 21, including a fourth set of flanges spaced from one another along the longitudinal axis of the base and radially aligned with one another about said longitudinal axis, wherein each flange of the fourth set extends from the base co-planarly with a respective flange of the second set, and wherein the flanges of the second and fourth sets are pie-shaped and each respective co-planar pair of flanges extend from the base on opposite sides thereof.

23. The dental appliance of claim 22, wherein the second and fourth sets of flanges are generally radially aligned with spaces between the first and third sets of flanges.

24. An interproximal dental appliance, comprising:
an elongated base configured for insertion into interproximal spaces between teeth; and
a plurality of elastomeric flat-faced flanges extending perpendicularly outwardly from the base in a staggered pattern, the flanges including a first set spaced from one another along a longitudinal axis of the base and radially aligned with one another about said longitudinal axis, and a radially aligned second set longitudinally disposed in an alternating manner between adjacent flanges of the first set along the longitudinal axis of the base, wherein the first set of flanges is radially offset from the second set of flanges;
wherein the base comprises a bi-material composite structure including a relatively stiff, resilient core, and a sheath over the core integrally formed with the flanges.

25. The dental appliance of claim 24, wherein the sheath encapsulates an end of the core and forms a flexible leader that is threadable into the interproximal spaces between teeth.

26. The dental appliance of claim 24, wherein the base includes a threadable leader at one end configured for insertion into interproximal spaces between teeth and a handle at a second end, and wherein the elastomeric flanges extend from the base between the threadable leader and the handle.

27. The dental appliance of claim 24, including a third set of flanges spaced from one another along the longitudinal axis of the base and radially aligned with one another about said longitudinal axis, wherein each flange of the third set extends from the base co-planarly with a respective flange of the first set.

28. The dental appliance of claim 27, including a fourth set of flanges spaced from one another along the longitudinal axis of the base and radially aligned with one another about said longitudinal axis, wherein each flange of the fourth set extends from the base co-planarly with a respective flange of the second set, and wherein the flanges of the second and fourth sets are pie-shaped and each respective co-planar pair of flanges extend from the base on opposite sides thereof.

29. The dental appliance of claim 28, wherein the second and fourth sets of flanges are generally radially aligned with spaces between the first and third sets of flanges.

30. The dental appliance of claim 29, wherein the flanges collectively form a generally cylindrical ribbed segment in a floss-type interproximal dental appliance, wherein the base extends beyond the cylindrical ribbed segment to the handle and to the threadable leader, and wherein the handle comprises a closed loop of the base.

31. The dental appliance of claim 29, wherein the flanges collectively form a generally frusto-conical ribbed segment, and wherein the base is generally frusto-conical.

* * * * *